United States Patent [19]

Przydrozny et al.

[11] Patent Number: 4,833,112

[45] Date of Patent: May 23, 1989

[54] THIORESISTANT CATALYST FOR METHANE PRODUCTION

[75] Inventors: Michel Przydrozny, Meriel; Roger D. D'Emmerez de Charmoy, Maisons Alfort; Guy N. L. Sauvion, Chevilly Larue; Jack J. R. Caillod, Taverny, all of France

[73] Assignee: Gaz De France, France

[21] Appl. No.: 207,300

[22] Filed: Jun. 15, 1988

Related U.S. Application Data

[60] Division of Ser. No. 077,694, Jul. 24, 1987, Pat. No. 4,774,261, which is a continuation of Ser. No. 812,179, Dec. 23, 1985, abandoned.

[30] Foreign Application Priority Data

Dec. 28, 1984 [FR] France ............................ 8420069

[51] Int. Cl.$^4$ .................. B01J 23/10; B01J 23/84; B01J 23/85; B01J 23/88
[52] U.S. Cl. ........................... 502/304; 518/714; 518/715
[58] Field of Search ............................. 502/304

[56] References Cited

U.S. PATENT DOCUMENTS 4,260,553 4/1981 Happel et al. .................. 502/304 X
4,540,714 9/1985 Pedersen et al. ............... 518/721 X

*Primary Examiner*—W. J. Shine
*Attorney, Agent, or Firm*—Steinberg & Raskin

[57] ABSTRACT

A method of methane production with a thioresistant catalyst wherein a mixture comprising in particular carbon monoxide, hydrogen and sulphur compounds is contacted with a thioresistant catalyst comprising a metal selected from the group comprising molybdenum, vanadium or tungsten and possible cobalt and/or nickel, this catalyst being deposited onto a cerium oxide support, the reaction being performed at a temperature lying between about 250° C. and 650° C. and at a pressure lying between about 5 bars and 140 bars. This method is useful to carry out the effective methane synthesis with a much improved selectivity in favor of methane.

2 Claims, No Drawings

THIORESISTANT CATALYST FOR METHANE PRODUCTION

This is a division of application Ser. No. 077,694, filed July 24, 1987, now U.S. Pat. No. 4,774,261, which is a continuation of application Ser. No. 812,179, filed Dec. 23, 1985, now abandoned.

BACKGROUND OF THE INVENTION

The present invention relates essentially to a method of production of methane or of a methane-containing gas mixture by means of a sulphur resistant or thioresistant catalyst.

It is also directed to the catalyst for carrying out this method.

It is already known to perform the synthesis of methane from a gas mixture comprising among other components carbon monoxide, hydrogen, water and sulphur compounds and said gas mixture may in particular be obtained through coal gasification and be contacted with a catalyst likely to activate the synthesis reaction.

For that purpose, various catalysts have been proposed but it has been found that they quickly become spent or exhausted or deactivated in view of the presence of sulphur compounds.

Thus, catalysts for the methanation reaction which which are based for instance on molybdenum and/or nickel deposited onto an alumina support have already been proposed but such catalysts are far from being very satisfactory with regard to their activity and their selectivity in favour of methane production.

SUMMARY OF THE INVENTION

Therefore, the object of the present invention is to cope with such inconveniences by providing a process of methane production with the assistance of thioresistant catalysts which give outstanding results with respect to the carbon monoxide conversion as well as to the selectivity in terms of produced methane and of the stability with time of the performances of the catalyst.

For that purpose, the subject matter of the invention is a process of production of methane or of a mixture comprising methane, from an initial mixture comprising in particular carbon monoxide, hydrogen and sulphur compounds, characterized in that said initial mixture is contacted with a thioresistant catalyst comprising a metal selected from the group comprising molybdenum, vanadium or tungsten and possibly an activity promoter consisting of cobalt and/or nickel, which catalyst is deposited onto a cerium oxide support at a temperature lying between about 250° C. and 650° C. and at a pressure lying between about 5 bars and 140 bars.

As will be seen later, the selectivity in terms of methane achieved by this method is much higher than that obtained with prior art methods owing to the essential fact that according to the present invention a catalyst deposited onto cerium oxide is used.

According to another characterizing feature of the process according to the invention, the reaction is accomplished at a space velocity (V/V/hr) lying between about 100 hours$^{-1}$ and 15,000 hours$^{-1}$ and with a hydrogen/carbon monoxide molar ratio equal to at least 0.3 and preferably equal to 1.

According to a preferred embodiment, the reaction is performed at a space velocity equal to 4,750 hours$^{-1}$ and with a hydrogen-to-carbon monoxide molar ratio equal to 1, at a pressure equal to 30 bars and at a temperature lying between 300° C. and 600° C. and preferably equal to 500° C.

The invention is also directed to a catalyst for carrying out the process meeting either one of the above characteristics, this catalyst being characterized in that it is represented by the formula $X/CeO_2$, $X/Co/CeO_2$, $X/Ni/CeO_2$ or $X/Co/Ni/CeO_2$ wherein X stands for molybdenum, vanadium or tungsten and in that it is defined by the following characteristics:

- a BET specific area of the $CeO_2$ support above 10 $m^2/g$,
- a total pore volume lying between about 0.15 $cm^3/g$ and 0.5 $cm^3/g$,
- a packed filling density lying between about 0.5 and 2.5,
- an atomic ratio of said X metal to cerium lying between about 1/50 and ¼, and
- an atomic ratio of the activity promoter metal (cobalt and/or nickel) to X metal lying between 0 and 1.

According to a preferred embodiment, the BET specific area of the above-mentioned catalyst is equal to 50 $m^2/g$, its total pore volume is lying between 0.3 $cm^3/g$ and 0.4 $cm^3/g$, the packed filling density is lying between 1 and 2, the X/cerium atomic ratio is lying between 1/20 and 1/7, and the promoter-to-X metal atomic ratio is lying between 0.1 and 0.5.

This catalyst may be prepared by conventional techniques and in particular through impregnation of the support with solutions of the precursors of those metals which are desirably added.

DESCRIPTION OF THE PREFERRED EMBODIMENTS

Further characterizing features and advantages of the invention will better appear in the following example which should not be construed as limiting the present invention.

Three catalysts deposited onto cerium oxide have at first been prepared, namely: a molybdenum/cerium oxide catalyst, a cobalt/molybdenum/cerium oxide catalyst and a nickel/molybdenum/cerium oxide catalyst.

The $Mo/CeO_2$ catalyst had a BET specific area of 42 $m^2/g$, a total pore volume of 0.14 $cm^3/g$, a packed filling density of 1.83 and a molybdenum content of 3.6% by weight.

The $Co/Mo/CeO_2$ catalyst had a BET specific area of 39 $m^2/g$, a water-porous volume of 0.11 $cm^3/g$ and a packed filling density of 1.92.

At last, the $Ni/Mo/CeO_2$ catalyst had a BET specific area of 37 $m^2/g$, a water-porous volume of 0.11 $cm^3/g$ and a packed filling density of 1.95.

Then, a catalytic test for comparing the performances of the three above-mentioned catalysts to known alumina or aluminum based catalysts and complying with the following formulae: $Mo/Al_2O_3$, $Co/Mo/Al_2O_3$, $Ni/Mo/Al_2O_3$ and $Ce/Mo/Al$ was carried out.

This catalytic test which had the purpose of comparing the performances of all the above-mentioned catalysts in terms of activity and selectivity in the preparation of methane consisted in contacting all these catalysts with a mixture of reagents comprising in a first stage (conditions of table 1) 37.25% by volume of CO (carbon monoxide), 37.25% by volume of $H_2$, 25% by volume of $H_2O$ and 0.5% by volume of $H_2S$ and, in a second stage (conditions of table 2) 49.75% by volume of CO, 49.75% by volume of $H_2$ and 0.5% by volume of $H_2S$.

The reaction was performed at a space velocity of 4,750 hr$^{-1}$ under a pressure of 30 bars and a temperature of 500° C. after the catalysts had undergone a pre-sulphuration treatment at 350° C. for 6 hours under a stream of 10 liters/hour of a mixture of 1.3% of H$_2$S in hydrogen.

After the separation of water by a condenser, the issuing gases were analyzed through gas-chromatography which made it possible to proportion in particular CO, CO$_2$, CH$_4$, C$_2$H$_6$ and C$_3$H$_8$.

This analysis has allowed computation of on the one hand the carbon monoxide conversion rate (%) defined by the ratio:

$$t_{CO} = \frac{\text{moles of consumed CO}}{\text{moles of added CO}} \times 100,$$

and, on the other hand, the selectivity in terms of CH$_4$(%) defined by the ratio:

$$S_{CH_4} = \frac{\text{moles of formed CH}_4}{\text{moles of consumed CO}} \times 100.$$

Tables 1 and 2 hereinafter show the results obtained with all the catalysts previously described before and after an ageing corresponding to 100 hours of operation or work of the catalyst.

TABLE 1

| Catalysts | | Before ageing | | After ageing | |
|---|---|---|---|---|---|
| | | $t_{CO}$ % | $S_{CH_4}$ % | $t_{CO}$ % | $S_{CH_4}$ % |
| Prior art | Mo/Al$_2$O$_3$ | 61.7 | 15.2 | 57.4 | 12.1 |
| | Co/Mo/Al$_2$O$_3$ | 62.6 | 24.8 | 61.6 | 19.1 |
| | Ni/Mo/Al$_2$O$_3$ | 66.7 | 22.3 | 65 | 18.5 |
| | Ce/Mo/Al | 71 | 21.9 | 64.8 | 20.8 |
| Invention | Mo/CeO$_2$ | 80.4 | 30.4 | 77 | 28 |
| | Co/Mo/CeO$_2$ | 87.3 | 36.7 | 81.1 | 32.7 |
| | Ni/Mo/CeO$_2$ | 88.1 | 35.3 | 81.5 | 31.9 |

TABLE 2

| Catalysts | | Before ageing | | After ageing | |
|---|---|---|---|---|---|
| | | $t_{CO}$ % | $S_{CH_4}$ % | $t_{CO}$ % | $S_{CH_4}$ % |
| Prior art | Mo/Al$_2$O$_3$ | 78.3 | 49.9 | 69.4 | 50.0 |
| | Co/Mo/Al$_2$O$_3$ | 79.1 | 50.0 | 70.9 | 49.5 |
| | Ni/Mo/Al$_2$O$_3$ | 78.8 | 49.6 | 71.9 | 49.8 |
| Invention | Mo/CeO$_2$ | 85.8 | 49.7 | 78.2 | 49.8 |
| | Co/Mo/CeO$_2$ | 87.1 | 50.0 | 78.7 | 50.0 |
| | Ni/Mo/CeO$_2$ | 86.6 | 48.0 | 79.0 | 47.3 |

The results given in table 1 clearly substantiate the superiority of the catalysts according to the invention over the prior art catalysts as to the carbon monoxide conversion rate, the selectivity in terms of produced methane and the stability with time of the performance.

More specifically, it should be pointed out that the Mo/CeO$_2$ catalyst is not only superior to the three first prior art catalysts containing no cerium oxide, but is also superior to the fourth prior art catalyst mentioned in table 1 and which is based on cerium, molybdenum and aluminum.

This superiority is also clearly seen with respect to the Co/Mo/CeO$_2$ and Ni/Mo/CeO$_2$ catalysts if the same are compared to the prior art catalysts and in particular to the Co or Ni catalysts with molybdenum deposited onto alumina. It is indeed seen here that with these two catalysts, a selectivity in methane lying between 32% and 36% and CO conversion rates above 80% are achieved.

The results given in table 2 (absence of water in the starting mixture) show that CO conversion rates above 85% and definitely better than those obtained with the prior art catalysts are achieved. The results are also better with respect to the stability with time of the performances.

The selectivity in terms of produced methane is substantially the same as that of the prior art catalysts and in any case lies at the thermodynamic limit.

There has accordingly been provided according to the invention a methanation process which allows recovery of substantial amounts of methane by using a very stable cerium oxide-based catalyst effectively resistant to sulphur compounds such as H$_2$S, COS, CS$_2$, CH$_3$S, etc. . . . and the content of which may exceed 4 molar percent of sulphur.

It should be understood that the invention is not at all limited to the embodiment or the example described hereinabove.

Thus, by replacing molybdenum with vanadium or tungsten in the formulae of the catalysts according to the principle of the invention, results and performances close to those described hereinbefore are obtained. Likewise, the joint use of two activity promoter metals (cobalt and nicke) instead of a single one would lead to a catalyst quite active in favour of methane production.

The invention therefore comprises all the technical equivalents of the means described as well as their combinations if same are carried out according to its substance.

What is claimed is:

1. A catalyst for the production of methane or a methane-containing gas mixture from a mixture of carbon monoxide, hydrogen and sulphur compounds, said catalyst being of the formula X/CeO$_2$, X/Co/CeO$_2$, X/Ni/CeO$_2$ or X/Co/Ni/CeO$_2$ wherein X stands for molybdenum, vanadium or tungsten and said catalyst being defined by the following characteristics:
   a BET specific area of the CeO$_2$ support above 10 m$^2$/g;
   a total pore volume between about 0.15 cm$^3$/g and 0.5 cm$^3$/g;
   a packed filling density between about 0.5 and 0.25;
   an atomic ratio of said X metal to cerium between about 1/50 and ¼; and
   an atomic ratio of the activity promoter metal (Co and/or Ni) to the X metal between 0 and 1.

2. A catalyst according to claim 1, wherein said BET specific area is equal to 50 m$^2$/g, said total pore volume is between 0.3 cm$^3$/g and 0.4 cm$^3$/g, the packed filling density is between 1 and 2, the X/cerium atomic ratio is between 1/20 and 1/7 and the promoter/X metal atomic ratio is between 0.1 and 0.5.

* * * * *